US005758641A

United States Patent [19]

Karr

[11] Patent Number: 5,758,641

[45] Date of Patent: Jun. 2, 1998

[54] CONTINUOUS-FLOW OXYGEN VALVE FOR OXYGEN REBREATHERS

[76] Inventor: Lawrence J. Karr, 445-15th St., Santa Monica, Calif. 90404

[21] Appl. No.: 748,020

[22] Filed: Nov. 12, 1996

Related U.S. Application Data

[60] Provisional application No. 60/006,846 Nov. 16, 1995.

[51] Int. Cl. 6 ........................ A61M 16/00; A62B 7/00; A62B 9/02; F16K 31/02

[52] U.S. Cl. ........................ 128/204.22; 128/205.24; 137/93

[58] Field of Search ........................ 128/201.28, 205.24, 128/204.22, 204.21, 205.11, 201.27; 251/129.06; 137/3, 93

[56] References Cited

U.S. PATENT DOCUMENTS

| | | | |
|---|---|---|---|
| 2,160,326 | 5/1939 | Carbonana | 128/204.22 |
| 2,770,231 | 11/1956 | Falk | 128/205.24 |
| 2,817,350 | 12/1957 | Bradner et al. | 128/204.22 |
| 3,252,458 | 5/1966 | Krasberg | 128/204.22 |
| 3,695,261 | 10/1972 | Emmons | 128/204.22 |
| 3,727,626 | 4/1973 | Kanursher et al. | 128/204.22 |
| 3,805,590 | 4/1974 | Ringwall et al. | 128/204.22 |
| 4,236,546 | 12/1980 | Manley et al. | 128/204.22 |
| 4,423,723 | 1/1984 | Winkler et al. | 128/204.22 |
| 4,602,653 | 7/1986 | Ruiz-Vela et al. | 128/205.11 |
| 5,076,267 | 12/1991 | Pasternack | 128/205.24 |

*Primary Examiner*—Kimberly L. Asher

*Attorney, Agent, or Firm*—Thomas I. Rozsa; Tony D. Chen

[57] ABSTRACT

A continuous-flow oxygen valve for oxygen rebreathers employs the use of reversible rotary motors to control continuously variable valves in order to provide more constant gas flow to oxygen rebreathers. The motor is connected by gears to a valve which can be adjusted over the appropriate control range necessary to maintain the optimum gas balance. Once the valve is adjusted, the amount of gas flowing through it remains constant until a subsequent adjustment is performed. The gas levels are measured by sensors and conditioning circuitry. Once the appropriate gas flow is computed by the unit control elements, the controller will cause continuous or pulsed current to flow through the valve motor until the flow is set at the appropriate level. Current will then cease to flow. When conditions cause the balance of the gasses to vary from the optimum level, the controller will again make an adjustment in the valve position.

8 Claims, 1 Drawing Sheet

CONTINUOUS-FLOW OXYGEN VALVE FOR OXYGEN REBREATHERS

This is a full patent application of copending provisional application Ser. No. 60/006,846 filed on Nov. 16, 1995.

BACKGROUND OF THE INVENTION

This is a Patent Application of a provisional application Ser. No. 60/006,846 filed on Nov. 16, 1995, now pending.

DESCRIPTION OF THE PRIOR ART

Oxygen rebreather apparatus have been used for underwater and hazardous atmosphere breathing applications for several decades. The principle of operation is that carbon dioxide is "scrubbed" from the breathing gas mixture by means of a caustic chemical reaction conducted in a fixed bed through which the gasses are passed. Oxygen content of the gas mixture is maintained by the addition of relatively small amounts of pure oxygen rather than with larger volumes of gas as are required for breathing compressed air.

This approach has several distinct advantages over systems using ordinary air. First, in underwater applications the gas mixture can be more carefully regulated allowing increased underwater time with far less danger of dangerous gas absorption. Surface rebreathers are far lighter than compressed air units and allow more breathing time and enhanced mobility. For military applications the telltale bubble trail evident with compressed air systems is not present and greater depths may be achieved safely.

Recent advances in the field have improved the ability to control the level of oxygen, but still have some shortcomings. Early devices simply regulated the breathing oxygen level to the ambient pressure. This led to high concentrations of oxygen and limited underwater depth to approximately 30 feet beyond which point the oxygen became toxic. Subsequent to these devices simple on/off servos were implemented using solenoid or other on/off valves. This approach was a significant improvement, but had the disadvantages of relatively inaccurate regulation, noise from the valves, and radiation of magnetic fields deemed troublesome by military users. Most recently, solenoid valves have been employed with means to supply the gas more constantly by varying the duty cycle of the valves which are opened on a regular schedule.

These approaches all have some disadvantages connected both with the solenoid valves and with the method of control. The technique of duty-cycle control can be made to approach continuous flow, but only by actuating the valve at increasingly frequent intervals. This wastes power, which is generally drawn from batteries, creates more noise, and increases the surrounding magnetic disturbance from the solenoid coil.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Figure 1:
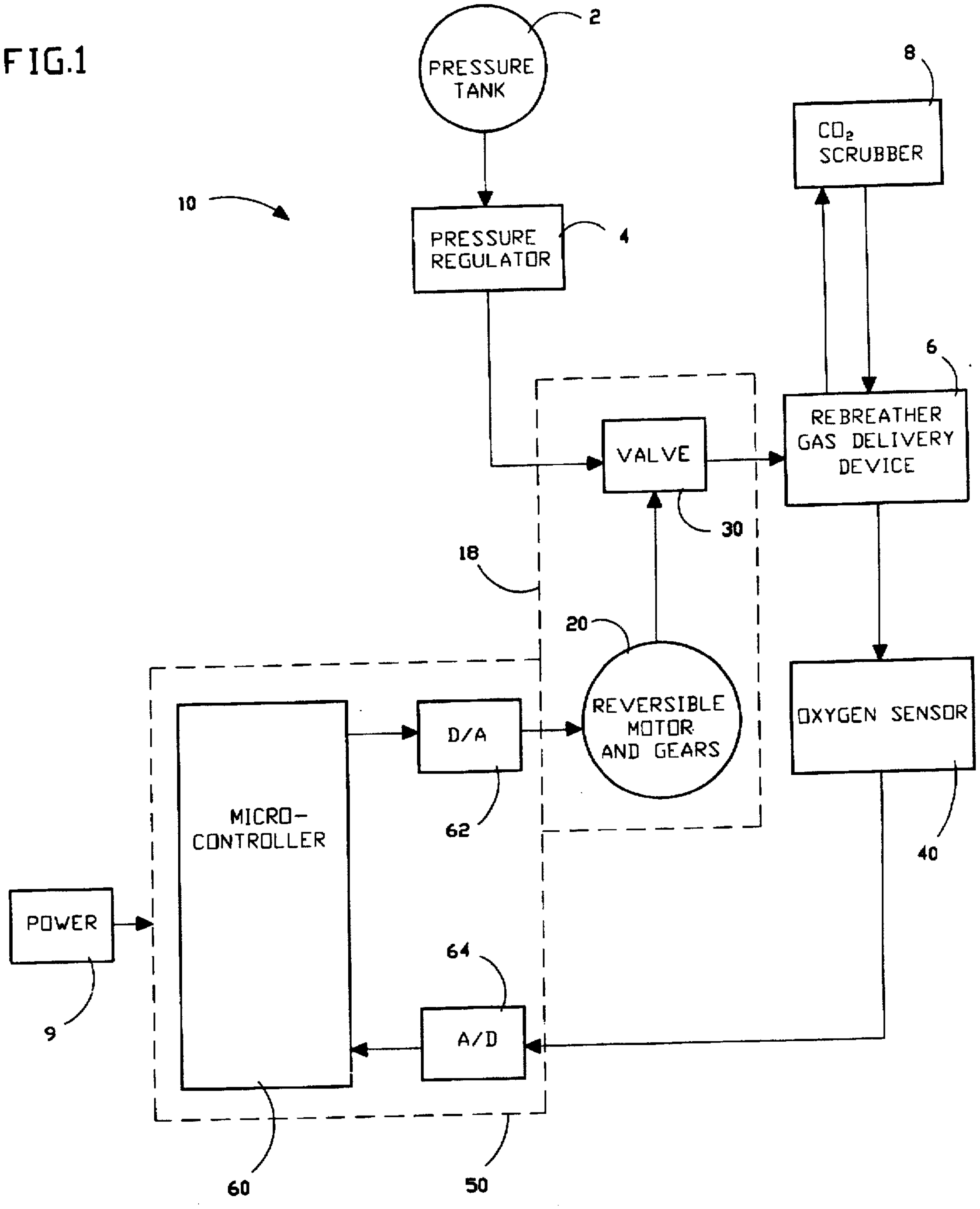
FIG. 1 is a block diagram of the present invention continuous-flow rebreather apparatus.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIG. 1, there is shown at 10 a block diagram of the present invention continuous-flow oxygen rebreather apparatus. The invention 10 disclosed here employs the use of reversible rotary motors 20 which may be electromagnetic, fluidic, or piezoelectric to control continuously variable valves 30 in order to provide more constant oxygen flow to oxygen rebreathers. In this system 10, the motor 20 is connected by gears or other suitable mechanical means to a valve 30 which can be adjusted over the appropriate control range necessary to maintain the optimum oxygen balance. The valve 30 is designed in such a manner that once adjusted, the amount of oxygen flowing through it remains constant until a subsequent adjustment is performed. In application, the oxygen level will be measured by suitable sensors 40 and conditioning circuitry 50. A control element 62 is used to control the motor 20 while a control element 64 measures the oxygen sensor output. Once the appropriate oxygen flow is computed by the microcontroller 60, the microcontroller 60 and the control element 62 will cause a continuous or pulsed current to flow through the valve motor 20 until the flow is set at the appropriate level. Current will then cease to flow. When conditions cause the balance of the oxygen to vary from the optimum level, the microcontroller 60 will again make an adjustment in the valve position as previously described.

This mechanism 18 has several distinct advantages. First, the flow of the oxygen is more constant and the regulation of the percentages of the constituent gasses is, as a result, more uniform. This is safer for the users and helps to limit oxygen peaks which (a) may be damaging to the user's lung tissues, and (b) may affect the central nervous system and cause convulsions. Second, power consumption is reduced by virtue of the fact that the valve 30 remains open without application of external power until the next adjustment is performed. The need for changes in the flow rate are relatively less frequent than the number of times the comparable solenoid valve must be activated, and, since the motors 20 have a more efficient structure, power consumption is markedly reduced. Third the noise of frequent solenoid operation is eliminated. Fourth size and weight can be reduced because the mechanism is more efficient. Fifth, with electrical motors the external magnetic field is greatly reduced compared with that of a solenoid, and with the piezoelectric or fluidic motors the magnetic field can be completely eliminated. A bi-directional, bi-phase piezoelectric motor comprises a preferred implementation which would allow simple digital control and extremely quiet, reliable operation without external magnetic fields.

The continuous oxygen rebreather apparatus 10 (which by way of example can be a United States Navy Mark 16 rebreather) may also include a pressure tank 2 for containing oxygen ($O_2$), a pressure regulator 4 for controlling the pressure of oxygen ($O_2$) from the pressure tank 2, a carbon dioxide ($CO_2$) scrubber 8 for removing the $CO_2$ from the rebreather gas delivery device 6, and a power source 9 for electrically powering the conditioning circuitry 50. These components are conventional in the art.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A continuous oxygen rebreather apparatus, comprising:

a. a pressure tank for containing oxygen ($O_2$);

b. a pressure regulator connected to said pressure tank for controlling the pressure of oxygen ($O_2$);

c. a rebreather device for delivering an appropriate amount of oxygen ($O_2$) to a user;

d. a carbon dioxide ($CO_2$) scrubber connected to said rebreather device for removing carbon dioxide ($CO_2$);

e. a continuously variable valve connected between said pressure regulator and said rebreather device for delivering a controlled oxygen flow to said rebreather device;

f. a reversible rotary motor having gears connected to said variable valve for adjustably controlling the amount of opening on said continuously variable valve in order to provide said controlled oxygen flow to said rebreather device;

g. an oxygen sensor connected to said rebreather device for measuring oxygen levels of said rebreather device;

h. a microcontroller connected between said reversible rotary motor and said oxygen sensor for controlling a current flow through said reversible rotary motor until the oxygen flow is set at an appropriate level, which said reversible rotary motor in turn sets the appropriate amount of opening on said continuously variable valve to maintain an optimum oxygen balance, and for causing said rotary motor to readjust said variable valve to reach the optimum level when balance of oxygen is varied from the optimum level; and i. a power source for powering said microcontroller and said reversible rotary motor.

2. The apparatus in accordance with claim 1 wherein said reversible rotary motor includes a bi-directional, bi-phase piezoelectric motor which allows simple digital control without external magnetic fields.

3. The apparatus in accordance with claim 1 further comprising a digital to analog (D/A) converter connected between said microcontroller and said reversible rotary motor.

4. The apparatus in accordance with claim 1 further comprising an analog to digital (A/D) converter connected between said microcontroller and said oxygen sensor.

5. A continuous-flow oxygen mechanism for use with a pressure tank which comprises oxygen ($O_2$), a pressure regulator which controls the pressure of oxygen ($O_2$), a rebreather device which delivers an appropriate amount of oxygen ($O_2$) to a user, a carbon dioxide ($CO_2$) scrubber connected to the rebreather device for removing carbon dioxide ($CO_2$), and an oxygen sensor which measures oxygen levels of the rebreather device, the mechanism comprising:

a. a continuously variable valve for connecting between said pressure regulator and said rebreather device and for delivering a controlled oxygen flow for said rebreather device;

b. a reversible rotary motor having gears connected to said variable valve for adjustably controlling the amount of opening on said continuously variable valve in order to provide said controlled oxygen flow for said rebreather device; and c. a microcontroller connected to said reversible rotary motor and being adapted to connect to said oxygen sensor for controlling a current flow through said reversible rotary motor until the oxygen flow is set at an appropriate level, which said reversible rotary motor in turn sets the appropriate amount of opening on said continuously variable valve to maintain an optimum oxygen balance and causing said rotary motor to readjust said variable valve to reach the optimum level when balance of oxygen is varied from the optimum level.

6. The mechanism in accordance with claim 5 wherein said reversible rotary motor includes a bi-directional, bi-phase piezoelectric motor which allows simple digital control without external magnetic fields.

7. The mechanism in accordance with claim 5 further comprising a digital to analog (D/A) converter connected between said microcontroller and said reversible rotary motor.

8. The mechanism in accordance with claim 5 further comprising an analog to digital (A/D) converter connected to said microcontroller and being adapted to connect to said oxygen sensor.

* * * * *